(12) United States Patent
Neuvonen et al.

(10) Patent No.: US 10,383,541 B2
(45) Date of Patent: Aug. 20, 2019

(54) COGNITIVE MAPPING USING TRANSCRANIAL MAGNETIC STIMULATION

(75) Inventors: Tuomas Neuvonen, Espoo (FI); Henri Hannula, Helsinki (FI); Gustaf Jarnefelt, Helsinki (FI)

(73) Assignee: Nexstim Oyj, Helsinki (FI)

( * ) Notice: Subject to any disclaimer, the term of this patent is extended or adjusted under 35 U.S.C. 154(b) by 794 days.

(21) Appl. No.: 13/824,409

(22) PCT Filed: Mar. 5, 2012

(86) PCT No.: PCT/FI2012/050218
§ 371 (c)(1),
(2), (4) Date: Apr. 24, 2013

(87) PCT Pub. No.: WO2012/117166
PCT Pub. Date: Sep. 7, 2012

(65) Prior Publication Data
US 2013/0338483 A1   Dec. 19, 2013

Related U.S. Application Data

(60) Provisional application No. 61/448,676, filed on Mar. 3, 2011.

(51) Int. Cl.
*A61B 5/00* (2006.01)
*A61B 5/055* (2006.01)
(Continued)

(52) U.S. Cl.
CPC .......... *A61B 5/055* (2013.01); *A61B 5/04012* (2013.01); *A61B 5/162* (2013.01);
(Continued)

(58) Field of Classification Search
CPC ................ A61B 5/055; A61B 5/4064; A61B 2560/0223; A61B 5/162; A61B 5/4803; A61B 5/04012; A61B 5/742; A61N 2/02
See application file for complete search history.

(56) References Cited

U.S. PATENT DOCUMENTS 6,425,852 B1 *   7/2002   Epstein .................. A61N 2/006
                                                          600/13
6,849,040 B2     2/2005   Ruohonen et al.
(Continued)

FOREIGN PATENT DOCUMENTS

CN   101516444 A    8/2009
CN   101517618 A1   8/2009

OTHER PUBLICATIONS

Ettinger et al. "Experimentation with a transcranial magnetic stimulation system for functional brain mapping", Medical Image Analysis, 2(2), pp. 133-142, 1998.*
(Continued)

*Primary Examiner* — Kaylee R Wilson
(74) *Attorney, Agent, or Firm* — Seppo Laine Oy

(57) ABSTRACT

The present invention relates to the field of mapping cognitive brain functions, more specifically to non-invasive systems for and methods of cognitive mapping. Examples of cognitive brain function which can reliably be mapped according to embodiments of the present invention are speech, language, working-memory and decision-making. According to certain embodiments, navigated Transcranial Magnetic Stimulation (TMS) is utilized along with accurate baseline determination in order to provide accurate, non-invasive cognitive mapping.

24 Claims, 5 Drawing Sheets

(51) Int. Cl.
A61B 5/04 (2006.01)
A61B 5/16 (2006.01)
A61N 2/02 (2006.01)

(52) U.S. Cl.
CPC .......... *A61B 5/4064* (2013.01); *A61B 5/4803* (2013.01); *A61N 2/02* (2013.01); *A61B 5/742* (2013.01); *A61B 2560/0223* (2013.01)

(56) References Cited

U.S. PATENT DOCUMENTS

| | | | |
|---|---|---|---|
| 7,440,789 | B2 | 10/2008 | Hannula et al. |
| 7,720,519 | B2 | 5/2010 | Ruohonen |
| 7,925,066 | B2 | 4/2011 | Ruohonen et al. |
| 2003/0073899 | A1 | 4/2003 | Ruohonen et al. |
| 2005/0033380 | A1* | 2/2005 | Tanner ............... A61B 5/05 607/45 |
| 2005/0075560 | A1 | 4/2005 | Hannula et al. |
| 2005/0107654 | A1* | 5/2005 | Riehl ............... A61N 2/006 600/9 |
| 2005/0256539 | A1* | 11/2005 | George ............... A61N 2/02 607/2 |
| 2006/0058853 | A1* | 3/2006 | Bentwich ............ A61N 2/006 607/45 |
| 2007/0106141 | A1 | 5/2007 | Hannula et al. |
| 2007/0294512 | A1* | 12/2007 | Crutchfield ........... G06F 8/443 712/200 |
| 2008/0058581 | A1 | 3/2008 | Aho |
| 2008/0058582 | A1 | 3/2008 | Aho et al. |
| 2008/0064950 | A1 | 3/2008 | Ruohonen et al. |
| 2008/0161636 | A1 | 7/2008 | Hurme et al. |

OTHER PUBLICATIONS eXimia NBS—An After Stroke Assistance in Rehabilitation. ladattu Oct. 7, 2015, kieli: venälä.
Fonyakin et al: "Cardiovascular Diseases and Cognitive Impairments. Prevention and Treatment", Neurology/Psychiatry. 2011, No. 9, p. 538.
Gimranov et al: "Transcranial Magnetic Stimulation: Estimation of the Motor System State in Patients with Brain Stem and Parastem Tumors", Burdenko Research Neurosurgical Institute, Accessed online Jul. 10, 2015.
Gimranov: "A Research of Phosphenes by Transcranial Magnetic Stimulation", 2003.
Gimranov: "An Interhemispheric Assymetry in Pathogenesis of Central Nervous System Disorders and Correction Thereof Via Transcranial Magnetic Stimulation", 2005.
Medgadget: "Nexstim NBS System 4 Delivers Transcranial Magnetic Stimulation for Depression and Stroke Rehab", www.medgadget.com, Dec. 2012.
A.T. Sack et al: "Imaging the Brain Activity Changes Underlying Impaired Visuospatial Judgments: Simultaneous fmRI, TMS, and Behavioral Studies", Cerebral Cortex, vol. 17, No. 12, Mar. 1, 2007.
Collignon O et al, "Reorganisation of the Right Occipito-Pariental Stream for Aditory Spatial Processing in Early Blind Humans. A Transcranial Magnetic Stimulation Study", Brain Topography, Kluwer Academic Publishers-Plenum Publishers, NE, vol. 21 No. 3-4, Feb. 6, 2009.
Corina D P et al: "Analysis of naming errors during cortical stimulation mapping: Implications for models for language representation", Brain and Language, Academic Press, San Diego, CA, US, vol. 115, No. 2, Nov. 1, 2010.
Driver J et al: "Concurrent brain-stimulation and neuroimaging for studies of cognition", Trend in Cognitive Sciences, Elsevier Science, Oxford, GB, vol. 13, No. 7, Jul. 1, 2009.
Irene Ruspantini et al: "The functional role of the ventral premotor cortex in a visually paced finger tapping task: A TMS study", Behavioural Brain Research, Elsevier, Amsterdam, NL, vol. 220, No. 2, Feb. 10, 2011.
Miniussi C et al: "Efficacy of repetitive transcranial magnetic stimulation/transcranial direct current stimulation in cognitive neurorehabilitation", Brain Stimulation, Elsevier, Amsterdam, NL, vol. 1, No. 4, Oct. 1, 2008.
Roosink M et al: "Corticospinal excitability during observation and imagery of simple and complex hand tasks: Implication for motor rehabilitation", Behavioural Brain Research, Elsevier, Amsterdam, NL, vol. 213, No. 1, Nov. 12, 2010.
Titova: Magnetic-resonance imaging of the brain. Mar. 30, 2009.
Troyanova I.M.: "Cognitive function as one of the important function of language", Vesmnuk TGPU, 2008. vol. 2 (76); pp. 56-58.

* cited by examiner

COGNITIVE MAPPING USING TRANSCRANIAL MAGNETIC STIMULATION

FIELD OF INVENTION

The present invention relates to the field of mapping cognitive brain functions. Examples of cognitive brain function which can reliably be mapped according to embodiments of the present invention are speech, language, working-memory, decision-making.

BACKGROUND OF THE INVENTION

While the anatomical structure of most individuals' brains is very similar, the functional arrangement of different individuals' brains are as unique as a fingerprint. This leads to the general problem in neuroscience that clinicians and doctors can easily identify abnormalities and traumas such as blood clots, tumors and stroke damage based on their understanding of brain anatomy. However, they currently have no way of visually determining the functions of the brain matter in and around those abnormalities and trauma.

Neurosurgeons are easily able to use existing technology such as MRI's to determine the location of a tumor in a patient's brain. Based on the location of a tumor a surgeon can plan what they think with be the best route for getting to and removing the tumor. However, what they cannot determine are things like how much brain matter around the tumor they can remove without substantially affecting the patient's functions, how the route to the tumor may go through critical areas which could easily be avoided by a different path, how the removal of the tumor will affect a patient's functions, etc.

One method Neurosurgeons have to mitigate some of these risks is direct electrical stimulation of the brain during surgery. By exposing a portion of a brain to an electrical current it is possible for the surgeon to make a judgment about the function of that portion of the brain. When testing for a motor response this can work well as it is easy to visually determine, or measure, a person's physical responses. For example, the assistant can see if the patient's finger moves in response to a stimulation.

Many drawbacks arise from such direct stimulation methods. For one, any time spent during surgery testing brain functions is taken away from the actual removal of a tumor or other surgical function. As patient risk is directly correlated to the length of a surgery, this is a factor that needs to be mitigated. Therefore there exists a clear need for a non-surgical method of accurately determining brain functions.

Another major drawback of current methods is that it is while it is relatively easy to test motor functions it is extremely difficult to accurately test cognitive functions. Therefore, there exists a need to accurately test one or more cognitive functions, such as, for example speech, language, working-memory, decision-making, etc.

Furthermore, while these problems exist and arise in the context of surgery and surgical planning, the use of an applicable solution can be extended to non-surgical situations. For example, during therapy it can be extremely useful to be able to accurately track progress or deterioration of cognitive functions. This can be helpful in both a clinical situation to test a patient's response to therapy as well as in a research situation to test if a therapy functions as it should.

SUMMARY OF THE INVENTION

An aspect of the present invention is to provide a system and method for mapping a cognitive function of subject. Cognitive functions can include, but are not limited to speech, language, working-memory, decision-making.

A further aspect of certain embodiments of the present invention is to provide a non-invasive system and method for accurately mapping a cognitive function.

According to certain embodiments of the present invention there are provided several methods of determining a cognitive base line response from a subject in response to the presentation of a task. In order to accurately map a cognitive function of a subject it is important to define an accurate baseline.

According to certain embodiments of the present invention there is provided a method comprising the step of presenting a task to the subject a subsequent time while stimulating an area of the brain. According to certain embodiments said stimulation is done in a non-invasive manner. An example of such non-invasive manner is with a magnetic field provided via a Transcranial Magnetic Stimulation (TMS) coil device.

According to certain embodiments of the present invention there is provided a method comprising the step of comparing one or more of a subject's base line responses to a task with the subject's later performance of a task during stimulation.

According to certain embodiments of the present invention there is provided a method comprising the step of determining if an area of a subject's brain which has been stimulated is involved in a particular cognitive function.

According to certain embodiments of the present invention there is provided a method comprising the step of presenting a task to a subject two or more times while correspondingly stimulating two or more areas of the brain. Certain embodiments are provided further comprising the steps of comparing the subject's base line response to the task with each of the subject's performances during stimulations, and determining if one or more of the areas of the brain stimulated are involved in the cognitive function.

Furthermore, according to certain embodiments of the present invention there is provided a method comprising one or more of the steps of presenting a task to a subject while stimulating the area of the brain with a magnetic field via a TMS coil device with a first set of parameters, wherein if no performance error is detected between the subject's base line and the subject's performance during stimulation, changing at least one of the parameters of the first set of parameters, and presenting the task to the subject while stimulating the same area of the brain with a magnetic field via a TMS coil device with the new set of parameters.

According to certain embodiments of the present invention there are provided systems which comprises a combination of at least some of the following components; a stimulation means, such as a Transcranial Magnetic Stimulation (TMS) coil device, a stimulus control connected to a TMS coil device capable of causing a TMS coil device to generate a magnetic field, a presentation display for presenting a task to a subject, at least one terminal having one or more processors, said one or more processors being configured to perform at least some of the steps of; determining, recording and/or inputting a cognitive base line response from a subject in response to the presentation of a task, presenting a task to a subject via, for example, a presentation display while stimulating an area of a brain with a magnetic field via, for example, a (TMS) coil device, comparing a subject's base line response to a task with the subject's performance during stimulation, and determining if the area of a brain stimulated is involved in a particular cognitive function.

Additional embodiments and aspects of the present invention are described in more detail herein.

DETAILED DESCRIPTION OF EXAMPLE EMBODIMENTS

Figure 1:
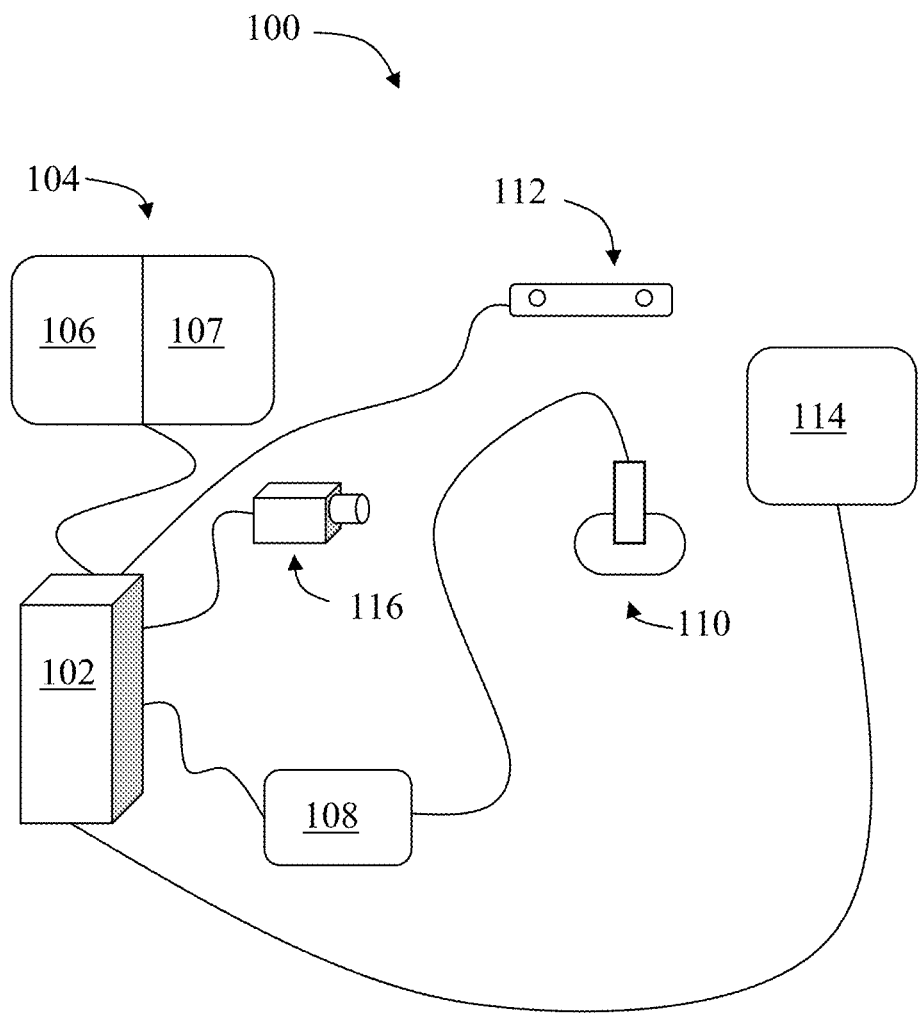
FIG. 1 shows an example of a system according to an embodiment of the present invention.

FIG. 1 shows an example of a system 100 which can be used in mapping cognitive functions of an individual. The system 100 is controlled by a terminal 102. Terminal 102 is shown directly connected to, and directly controlling, an operator display 104, a Transcranial Magnetic Stimulator (TMS) 108, a tracking system 112, a subject display 114, and a subject camera 116. Terminal 102 controls several additional functions and components, e.g. the TMS coil device 110.

Navigated Brain Stimulation (NBS) Navigation

Navigated Brain Stimulation (NBS) is the stimulation of specific locations or areas of an individual's brain. The stimulation can be created in a plurality of ways, the preferred non-invasive method being by generating magnetic fields which induce the stimulation in a specific location of a subject's brain. In order to map a portion of a subject's brain functions, the specific location of any stimulation should be accurately known. Therefore, NBS utilizes a tracking system such as 112 and tracking software in order to know the location of the stimulating device 110, or at least the relative location of the stimulating device 110 in relation to a subject's head and/or brain.

Several methods are known in which the location of a stimulating device 110 can be determined and several are described in more detail at least in US 2008/058582, "Transcranial magnetic stimulation induction coil device with attachment portion for receiving tracking device" which is herein incorporated by reference. At least some of these methods include tracking markers on or attached to the stimulating device 110. Additionally, markers can be attached to one or more locations on a subject's head, as described for example in US 2005/075560, "Stereotactic frame and method for supporting a stereotactic frame" which is herein incorporated by reference.

When markers are used in the tracking of the stimulation device 110 and/or the subject's head, a tracking system 112 is utilized which is capable of recognizing at least some or all of the markers. For example, if the markers used are capable of reflecting infrared light, then the tracking system 112 is an infrared tracking system or at least incorporates an infrared tracking system. Such an infrared tracking system can include one, two or more infrared tracking devices, such as infrared cameras, which are able to spatially locate the tracked objects in a 3D environment.

Other methods of tracking the stimulation device 110 and the subject's head are described in the aforementioned publications. In addition, one of ordinary skill in the art will recognize methods of tracking objects which can be utilized with the present system without departing from the scope of the present invention. Such methods include, for example, a tracking system 112 which includes at least one camera capable of capturing and/or recording, for example, visible light and tracking visual markers, light reflective markers, LEDs and/or objects themselves.

In certain embodiments, there is a single tracking system 112 which tracks both the stimulation device 110, the subject's head and any other desired tracked object(s). In certain other embodiments, more than one tracking system 112 is utilized for tracking a certain object or one or more objects have their own tracking systems (not shown). Information from the tracking system(s) is then sent either directly or indirectly to NBS navigation software.

Tracking data from the tracking system 112 is input to NBS navigation software which is then able to display NBS information on a NBS portion 106 of an operator display 104. The NBS display 106 is preferably capable of showing an operator the location of the stimulation device 110 in relation to the subject's head. Additionally, the NBS display 106 can utilize at least one anatomical model, e.g. a model of the subject's head, to show actual stimulation locations on a subject's brain and/or projected stimulation locations based on at least the location of the stimulation device 110. Examples of anatomical models are the subject's CT, the subject's MRI, a similar subject's CT or MRI or a standard head. U.S. Pat. No. 7,720,519, "Method for three-dimensional modeling of the skull and internal structures thereof", herein incorporated by reference, discloses several methods for selecting and utilizing anatomical models in NBS navigation.

NBS navigation software is capable of showing the stimulating tools as rigid objects, and showing predicted brain activation by modeling in real-time or off-line the electromagnetic properties of the coil and the subject's head. These models can be obtained by applying known bioelectromagnetic methods, such as spherical modeling, a boundary element method or a finite element method. Some additional functionality is described in more detail with regards to example embodiments and also in U.S. application Ser. No. 11/853,232, "A method for visualizing electric fields on the human cortex for the purpose of navigated brain stimulation" and Ser. No. 11/853,256, "Improved accuracy of navigated brain stimulation by online or offline corrections to co-registration" both of which are herein incorporated by reference. Furthermore, those of ordinary skill in the art will recognize modifications to the NBS navigation software and tracking system described herein which does not depart from the scope of the present invention.

Stimulation Device

A stimulation device 110 is used to stimulate specific portions of a subject's brain. In the present embodiments, the stimulation device 110 is a magnetic stimulation coil device which creates magnetic fields capable of electrically stimulating portions of a subject's brain. The magnetic stimulation coil device 110 itself normally comprises one or two wire coils, which when a current is passed through the coil(s) generates a desired magnetic field. Examples of suitable stimulation devices are described in US 2008/058582, "Transcranial magnetic stimulation induction coil device with attachment portion for receiving tracking device" and US 2008/058581, "Transcranial magnetic stimulation induction coil device and method of manufacture" both of which are herein incorporated by reference.

Stimulus Control

The stimulus control generally comprises a device which sends pulses to the stimulation device and stimulus control software. The stimulus control device can be, for example, a Transcranial Magnetic Stimulator (TMS). The TMS can contain a self contained operating and stimulus control program or stimulus control can be handled in another part of the system, e.g. on its own terminal or on a shared terminal.

Stimulus control software controls parameters such as the timing, intensity, pulse mode, pulse number, pulse frequency etc. Any or all of the parameters can be controlled automatically by the system, individually controlled by an operator or combination thereof. The stimulus control can have several inputs and be controlled in part by more than one controller. For example, the stimulus control can be controlled in part by an operator, a navigation control, and safety parameters. Some examples of stimulus control can be found in U.S. Pat. No. 6,849,040, "Method and apparatus for dose computation of magnetic stimulation" which is herein incorporated by reference.

Subject Physical Response Monitoring

During brain stimulation and mapping several different types of subject physical responses can be measured. One physical response monitoring solution is to use an EMG attached to a portion of the subject's body, e.g. finger. Another solution is to attach one or more electrodes (EEG, ECG, galvanic skin response) to the users body, for example as described in U.S. Pat. No. 7,440,789, "Electrode structure for measuring electrical responses from the human body" which is incorporated by reference herein. Yet another solution is to record vocal responses from the subject using a microphone. Yet another solution is to record subject behavior with a digital video camera. Furthermore, a combination of any of these solutions, or other applicable solutions, may be utilized.

Cognitive Stimulation Program

A cognitive stimulation program includes at least one, but preferably a set of presentation material which will be presented to a subject instructed to perform a task associated with the material. The presentation material can be, for example, a single picture, single pictures, groups of pictures, videos, audio clips, text etc. In addition to the presentation material the cognitive stimulation program includes control parameters for presentation of the material such as display time, inter-picture intervals, picture TMS intervals, counters, etc. Control parameters can be tied to individual presentation material, groups of presentation material, specific individuals, groups of individuals or other set groups. The cognitive stimulation program can also include instructions and/or a computer program which presents the presentation material preferably in accordance with at least one control parameter.

According to certain embodiments of the present invention, the cognitive stimulation program comprises a set of pictures and/or images, hereafter referred to simply as images. The total set can include as many, or more than, for example, 1000 images. For any one subject, the cognitive stimulation program may select between, for example but not limited to, 100-150 images to initially display to the subject. The initial number of images shown to a subject can be a predefined number or it can be determined when a predefined criteria is met. For example, a predefined criteria can be the subject correctly identifying a predetermined number of images, e.g. if the predetermined number is 50 and the subject identifies the $50^{th}$ correct image on the $165^{th}$ image shown then the initial set of images would be 165.

Cognitive Task

The subject is instructed to wait for a cue and when the cue is presented the patient is requested to perform a predefined task (e.g. counting aloud, speaking, naming an image). Time locked to the task performance, the stimulating device will deliver stimulation in an attempt to modulate (enhance, disturb or completely interrupt) the task performance. The task is preferably performed several times to gain certainty about the involvement of the stimulated brain area in the task performance and to reduce the occurrence of false positives and negatives.

Subject Cognitive Response Monitoring

The system may include a response device that the operator uses to annotate the experiment. Alternatively, the system may include a module that annotates the experiment records based on automatic detection of e.g. speech onset latency or other physical response recorded. The automated detection may be applied on video recording, audio track, readings from a physiological probe etc.

Session Recording

Session data is stored in multiple ways. All stimulation parameters (coil position, orientation and stimulation intensity parameters) can be stored by the NBS. Additionally, a video or audio trace can be recorded to facilitate the interpretation of transient and possibly unclear effects. Additionally any biosignal can be recorded and associated with stimulation parameters and coordinates.

FIG. 1 shows an embodiment of a system 100 which is predominantly self-contained. A single terminal 102, which can be, for example, one or more computers, contains the navigation control, stimulus control, cognitive programming, and at least initial session recording storage. Inputs to the system include the tracking device 112 which is an input to at least the navigation control programming, the camera 116 and optionally a microphone (not shown) which is at least an input to the session recording, any subject physical response monitors (not shown) such as EMG device(s), electrodes, etc., and operator inputs (not shown) such as one or more keyboards, pedal inputs, touch screen, etc. which allow operator control of some or all of the system.

Outputs from terminal 102 include the operator display 104, the subject display 114, and the TMS 108. The operator display 104 can be, for example, one or more computer displays which preferably displays at least an NBS display 106 showing, for example, a head model, previous stimulation locations and/or outcomes, projected stimulation locations, projected intensity, mapped areas, locations to be stimulated, stimulation parameters, etc. Additionally, it is preferable that the operator also has a subject response display 107 which displays at least the subject's physical responses to any stimulation, e.g. EMG display. The display can also display subject's cognitive responses or indications of a subject's cognitive responses, current or recent presentation material, as well as general system controls. Subject display 114 preferably is primarily used to display the presentation material to the subject. The subject display 114 can be, for example, a computer monitor, television, speaker or combination thereof. TMS 108 is further connected to the stimulation device 110.

A terminal 102 as shown may have one or more dedicated portions for controlling aspects of the system 100. For instance, one dedicated section can comprise dedicated inputs, processor(s) and storage media(s) containing navigation software. Said dedicated section then is responsible for controlling the navigation and can have one or more outputs to another or other sections of terminal 102 for utilizing the navigation. Similarly, there may be a dedicated section for the cognitive software package, session recording, system operation, etc.

Figure 2:
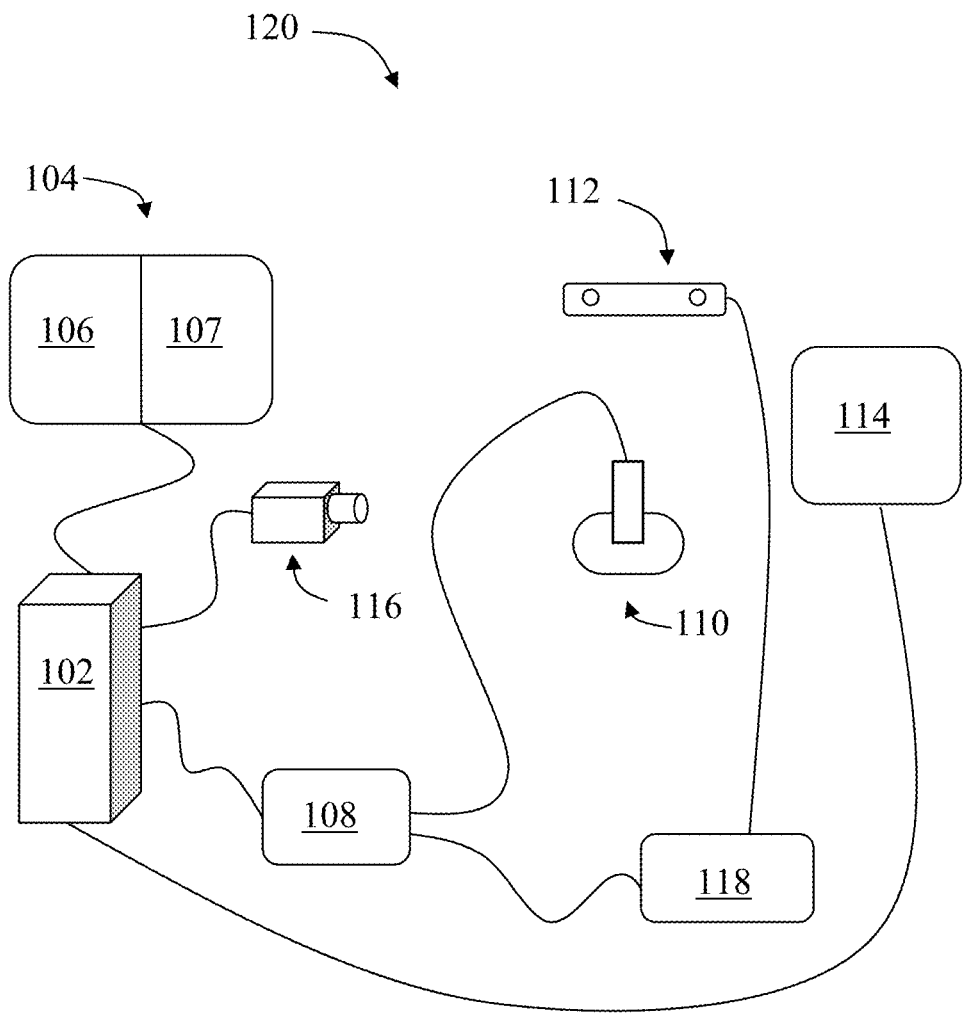
FIG. 2 shows another example of a system according to an embodiment of the present invention.

FIG. 2 shows a system 120 which is similar to that of system 100 in FIG. 1 except there is a dedicated NBS device 118 connected directly to the tracking device 112 and to the TMS 108. The NBS device 118 can contain a one or more processors/controllers and a navigation program stored on a computer readable medium. Additionally, NBS device 118 can contain a storage medium for storing navigation information. Navigation information can include past or recent stimulation locations, recent stimulation device 110 locations, and other information relevant to or determined by the navigation.

Removable storage mediums (not shown) can be used with the system. Some or all of the stored information relating to a subject, or group of subjects, can be stored on one or more removable storage mediums, such as a CD-ROM, DVD, thumb drive or external hard drive. Terminal 102 can also communicate with an intranet, internet, server or other terminal which can store, have stored there on, and/or have access to some or all of the system control programming or subject information.

Numerous variations of the systems presented in FIGS. 1 and 2 are possible without departing from the scope of the present invention. For instance, the NBS device 118 and the tracking device 112 can be contained in a single housing. NBS device 118 can additionally be connected directly to terminal 102 or, connected directly to terminal 102 and tracking device 112 but not directly to the TMS 108. Additionally, although the connections are shown in the figures as wires, at least some of the connections can be wireless.

A system in accordance with FIGS. 1 and 2 can be used, for example, in a clinical environment to map cognitive brain functions before or after surgery or another treatment. One example is if a subject has, or is suspected of having, a brain tumor in or around areas of speech functions in the brain. The system can be used in a clinician's office, doctors office, or pre-operating room to map the areas of the brain near the tumor that perform necessary speech functions. This data can then be exported, either taken on a removable storage medium or electronically sent, to a surgeon or operating room so that the surgeon can known what portions of the brain should be avoided to leave the patient with the most speech function possible after the surgery.

An advantage to the present example is that the system is capable of mapping the cognitive functions in 3-dimensional space without requiring physical access to the brain. Therefore, the clinician can spend as much time as necessary, possibly even over several sessions, to properly map the desired area of the brain. Then, during surgery the surgeon does not have to spend valuable time initially mapping brain function as they can have or can import the detailed mapped data of the particular portion of the brain.

A general use for certain embodiments of the present invention is to determine a volumetric for avoidance and/or safety during an invasive procedure. In many instances, in order to be of the most use it is preferable to have a volumetric having a resolution on the order of 1 $cm^3$. Mapping data can generally include two kinds of indicated data for a tested location, positive cognitive response or negative cognitive response. For example, the mapping data can indicate for a particular 1 $cm^3$ portion that said portion is required for speech (as speech was affected during stimulation of that portion or a neighboring portion or portions) or not required for speech (as speech was not affected during stimulation of that portion or one, more or all neighboring portions). In such instances, the negative cognitive response data may be more accurate than the positive cognitive response data. As such, non-speech or non-cognitive response data can be the primary, main or only mapping data shown and/or used for surgery or surgery planning.

Additionally, 3-dimensional cognitive mapping data from the system can be combined and/or integrated with surface or 3-dimensional mapping of the brain during surgery. In such an embodiment, once a portion of the brain or tumor is removed and then brain conforms to the portions absence (a phenomenon known as the "brain shift"), the mapping data can correlate the 3-dimensional cognitive data to the new brain configuration so that the cognitive functions of the brain in its new configuration can still be known based on the original cognitive mapping data.

Figure 3:
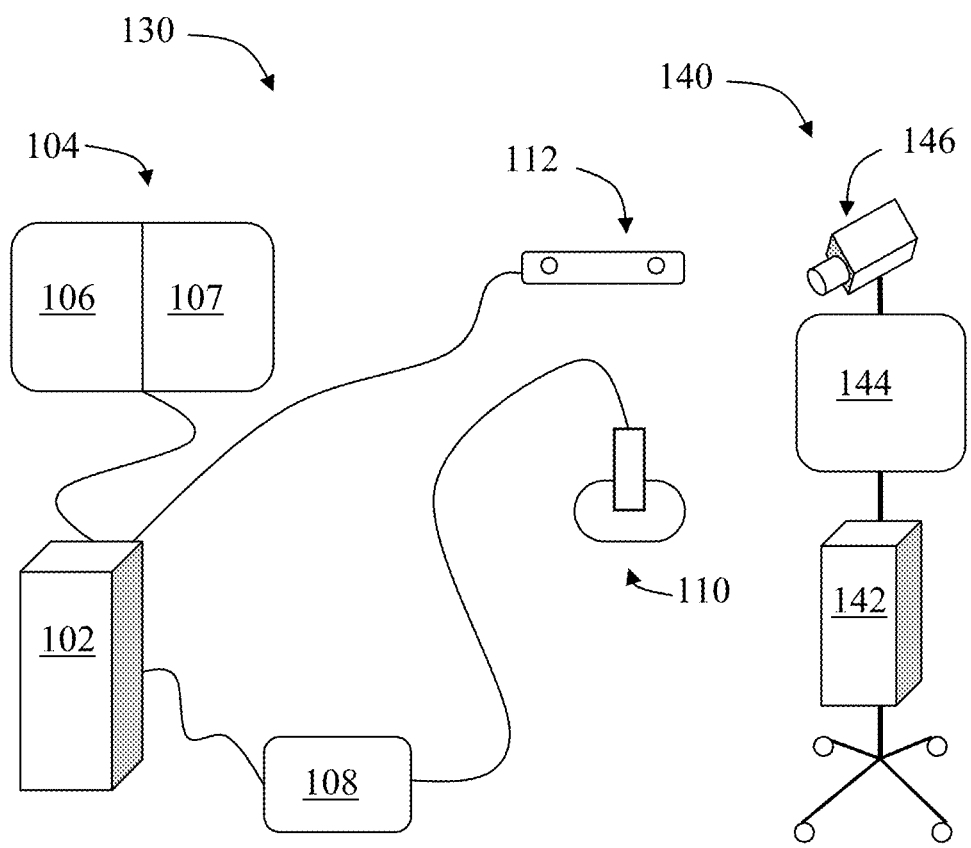
FIG. 3 shows another example of a system according to an embodiment of the present invention which includes a separate cognitive package.

FIG. 3 shows an embodiment having a first portion of the system 130, which is similar to that as described with respect to FIGS. 1 and 2, but with a second portion of the system 140 separate from the first. System 130 contains a terminal 102, operator display 104, TMS 108, stimulation device 110 and tracking device 112. System 130 can be a standard Transcranial Magnetic Stimulation system capable of magnetic brain stimulation and/or Navigated Brain Stimulation and/or brain function mapping.

System 140 is a cognitive package which in connection with, either wired or wireless, system 130 is capable of cognitive brain mapping through Transcranial Magnetic Stimulation. The cognitive package is comprised of a cognitive terminal 142, a display 144, and a recording device 146. Cognitive terminal 142 can be similar to terminal 102 as described above for the control of the cognitive program. Similarly, display 144 and recording device 146 can be similar to subject display 114 and camera 116 respectively as described above.

In the present embodiment, cognitive package 140 is shown on a medical stand and is preferably mobile. An advantage to the present embodiment is that a single cognitive package can be used with several different TMS or other systems. Similarly, several different cognitive packages can be used with a single TMS system. A cognitive package can, for instance, be brought from pre-op mapping in to an operating room to map cognitive functions or check mapping of cognitive functions immediately prior to, during and/or immediately after an operation.

A cognitive package 140 can also be used in with other types of brain stimulation systems and methods.

Cognitive package 140 can communicate directly with one or more portions of a system 130. For example, the cognitive terminal 142 can communicate directly with terminal 102 in a similar manner as if it were a distinct portion of the same terminal. Cognitive terminal 142 may also communicate directly with the TMS 108 and/or the NBS 118. Additionally, either terminal 102 or cognitive terminal 142 can be the primary controller of the system.

In one example, cognitive package 140 is placed in front of a subject so that the subject can view the material presented on the display 144. The operator is then capable of controlling the cognitive package through terminal 102 of system 130. Once the operator initiates a stimulation sequence from system 130, cognitive package 140 may operate autonomously until the end of the stimulation sequence. During autonomous operation, cognitive terminal 142 can directly control and/or trigger TMS 108 or it can send instructions to terminal 102 to control and/or trigger TMS 108. Similarly, NBS 118, or the NBS portion of terminal 102 may interact directly with cognitive terminal 142 or through instructions from terminal 102.

Figure 4:
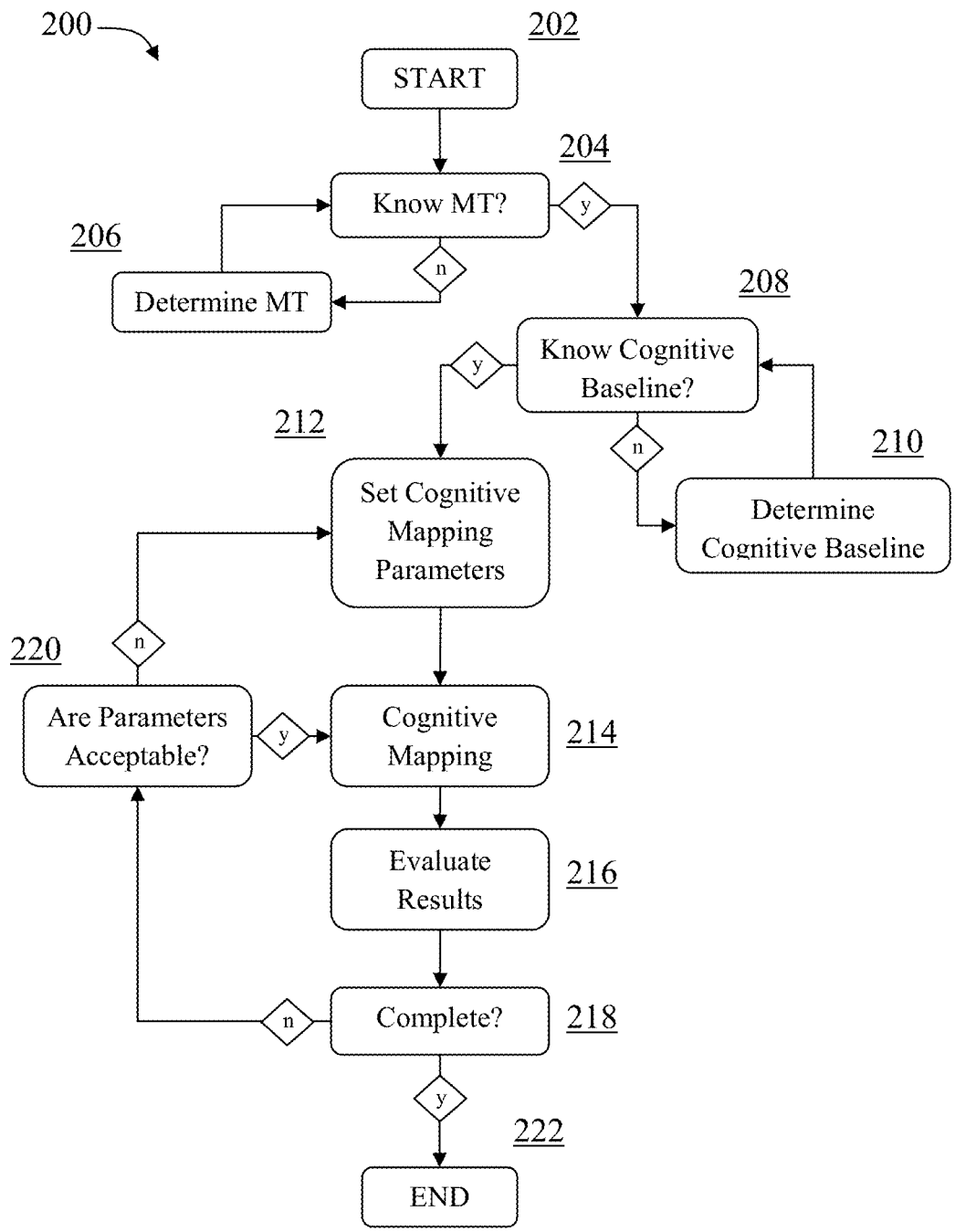
FIG. 4 shows a high level flow chart or a method for speech mapping according to an embodiment of the present invention.

FIG. 4 shows an example method 200 of mapping cognitive function. The method begins 202 with setting up the patient/subject in the system. This typically involves attaching any necessary physical monitoring devices and tracking objects to the subject. Additionally, this step can include calibrating the tracking device, tracking objects, tracking system, physical monitoring devices, displays and/or other necessary system components. The operator can optionally enter or load subject and/or session information such as bibliographic information, location, date, time etc.

At the start of the method 202, an operator can also chose an anatomical model to be used in the navigation. They can chose a pre-loaded anatomical model such as a standard head, a head model similar to the subject's or the subject's own anatomical model as described above. At this stage, the operator can also load the subject's own anatomical model or create an anatomical model for the subject from, for example, an MRI or CT. The chosen anatomical model is then preferably displayed in the NBS display section 106 of the operator's display 104.

Once all necessary calibrations are conducted and basic information entered, the operator should be able to see at least the subject's anatomical model and representation of the stimulation device 110 relative to the head model on the NBS display section 106 of the operator's display 104. The operator should also be able to see at least the output from the physical response monitor(s), e.g. EMG display, on, for example, portion 107 of display 104.

In step 204 it is determined whether the subject's motor threshold (MT) is known. If the subject has undergone TMS and knows their MT then the operator can enter the subject's MT via an input device, e.g. keyboard or touch screen. Additionally, if the subject or operator has a removable storage medium or other access to the patient's MT, said storage medium or information can be loaded at this time, if not already loaded. An operator can then test the MT value to check for its accuracy or can proceed directly to step 208.

If the subject's MT is, for instance, not known, not available or the given value is unreliable, then the operator can proceed to determine the subject's MT 206. Numerous methods of determining MT are known. For example, the operator can perform a series of stimuli and manually adjust TMS parameters, timing and intensity, and monitor display 107 until the MT is determined. Another example is the operator can be directed by programming to stimulate selected locations on the anatomical model at selected parameters (either manually adjusted or automatically adjusted) and monitor display 107 until MT is determined. Furthermore, the system can also include programming which is capable of determining the MT.

While step 204 is described with respect to MT in the present embodiment, other thresholds can be used in place of the MT. Thresholds such as the speech arrest threshold, e.g. the stimulation threshold which causes speech arrest or interruption in a task, can be used in conjunction with or in place of the MT. An excitability index, for example determined from an EEG for the brain area(s) outside of the motor system, such as for areas responsible for specific cognitive functions, can also be used as a threshold in this sense. In many embodiments, a threshold is determined or entered in order to be used as a stimulation level, e.g. intensity, starting point for cognitive mapping and/or as an input to the determination of a stimulation level starting point, e.g. default parameter for the subject. Therefore, other thresholds which can be used as or to determine a suitable or preferable stimulation level starting point can be used in conjunction with or in place of the MT and speech arrest thresholds.

Once the subject's MT is in the system then it can be determined if the cognitive baseline is known 208. For example, if the system is used for speech mapping then the cognitive baseline would be the speech baseline. A speech baseline is at least in part a measure of the subject's capacity to perform the requested task in relation to the presentation material, the subject's response time from seeing/hearing the presentation material without TMS or combination thereof. Additional information which can make up a subject's speech baseline include number of errors made during the baseline. The remainder of the method will be described with respect to the cognitive function being speech although the method can be used for mapping other desired cognitive functions as discussed above.

If the subject's speech baseline is not known then it is determined 210. Several methods of determining and/or recording a subject's baseline are possible. In one example, the cognitive display 114, 144 displays all of the presentation material which is to be used in the speech mapping in a sequential order. If the presentation material is a series of still photographs or images, then each will be presented and the subject's response is noted, measured and/or recorded.

In order to achieve the best mapping results, the presentation material should be clear to the subject and the subject's responses should be clear to the operator. For instance, if an image is shown and the subject does not recognize the image or the subject matter of the image then that image can be removed from the set of presentation material to be used during mapping. Similarly, if the subject is not sure what the image is or provides more than one name for an image, the subject's choice of names can be noted/recorded or the image can be removed. For example, if a picture of a car is used one subject's response can be to name the make and model of the car and another subject's response can be "car". If the desired response is "car", then the first subject's response can be noted/recorded or the picture can be removed from the set of presentation material.

In one example, an operator can control the baseline determination step 210 by manually selecting when presentation material is displayed and determining if certain portions of the presentation material should be removed from the set of presentation material. The operator can also enter other information or edit parameters during the determination step. However, when the timing of a subject's response is to be captured for the baseline determination it is useful to utilize a recording device for at least a portion of the baseline determination.

During determination of the subject's baseline, recording device 116, 146 can be utilized to record and/or measure the subject's baseline responses. Said recording device, e.g. camera, can alone or in conjunction with timing and/or cognitive programming determine the subject's response time to each piece of presentation material. Additionally, said recording device may also track, record and/or determine the subject's responses and in connection with the cognitive programming determine the subject's baseline with little or no operator input.

An important part of accurately mapping cognitive functions is establishing an accurate baseline for the subject. According to certain embodiments of the present invention, the baseline is a subject's ability to correctly and repeatedly perform a task without external brain stimulation. Because many subjects in need of such mapping have suffered from some sort of external or internal brain trauma, establishing an accurate baseline can be difficult and time consuming.

According to certain embodiments of the present invention, the task a subject is asked to perform is to identify a plurality of images with a relatively short space between images. The following examples are illustrative of methods for accurately determining a baseline for the subject as well as a useful set of images for use during cognitive mapping.

In a first example, a subject is shown a plurality of images at predetermined intervals, e.g. with 0.1-5 second intervals. The plurality of images can be a full set of images or a subset of a full set of images. In practice, showing an initial set of images ranging from 100-150 images has been sufficient to generate an acceptable size set of images to be used during cognitive mapping.

When an image is presented to a subject for the first time the subject can, for instance, identify the image within an acceptable amount of time, hesitate before answering, incorrectly identify the image, not answer, become frustrated by not being able to answer, have difficulty choosing between multiple answers for the image and so on. In certain embodiments, it is preferable to make a recordation about the subject's actual answer as well as possibly the manner in which they answered. This can be done in any number of ways. Since there is no stimulation occurring during the base line calculations there can be a visual and/or voice recording of the subject's response. This response can then be stored in a short or long term memory of the system along with the corresponding image. Additional methods of recording including the use of voice recognition software in order to save a text version of the subject's verbal answer with the corresponding image and/or manual entry and/or checking of the subject's answers and/or manner of answering can be used as well. One of ordinary skill will realize other alternatives of recording and/or storing the subject's response (answer and manner of answering) which do not depart from the scope of the present invention.

In most situations, if a subject is unable to properly identify an image, hesitates for a relatively lengthy period of time, is unable to select a single answer for the image or in another way cannot clearly identify the image in an acceptable period of time, that corresponding image is removed from the set of images to be used during cognitive mapping. Hesitation is a difficult problem to quantify as different people take different lengths of time to perform the same task. Therefore, according to certain embodiments of the present invention, a full set of initial images is shown to the subject and the subject's response recorded before discarding images from the set of images to continue with. In such embodiments, the system and/or operator can select a set of images which corresponds to the most successful responses from the subject. The set can be a predefined number of images or simply all or a portion of those images with the best responses.

In certain embodiments, once the initial set of images has been shown and images having unsuccessful responses have been discarded, the process repeats itself for one or more additional cycles. In certain embodiments, receiving at least 3 successful and identical responses from a subject to a particular image is required for an image to be usable in the final set of images to be used during cognitive mapping. However, the number of necessary, successful responses and the degree of similarity between the responses can be varied based on the condition of the subject and/or other environmental factors.

When a subject is shown an image for a second or subsequent time, their responses can be the same as described above with respect to the first time the saw the image or it may differ. The difference can occur, for example, in the time required for the subject to respond or the answer itself. For example, a subject might see an image and respond 'cup' the first time and 'mug' the second time. While both would be acceptable answers on their own, the fact that the user changed responses, without stimulus, known as semantic error, can often be a reason for discarding the image.

Determining semantic error can be accomplished in several ways. In certain embodiments, a subject's prior response, or portion of their response, is displayed and/or presented to the system operator. As an example, if the system employs voice recognition software then the word the system recognized from one or more previous responses is displayed for the operator. Simultaneously or alternatively, the system might play, for example through a head set, the users one or more previous responses for the operator. A determination can then be made, by the system, operator or combination thereof if the responses are similar, different or identical. Similarly, an operator can key in the initial response of the subject and simply indicate via a simple check box or similar input if subsequent responses match or do not match the initial response. Such a system can also be fully automated and may or may not include an operator check or confirmation of a similarity or difference. Certain embodiments may or may not include a display or presentation to the operator of an initial and/or one or more of a subject's previous responses or portions of said responses.

In certain embodiments of the present invention, the operator is shown both the previous image which was displayed to the subject and the current image. This allows some extra time for the operator to make and/or record any observations about the subject's response to the previous image. Likewise, in certain embodiments the operator may be shown more than just the previous image (e.g. additional previous images, images with responses that have not been fully recorded, upcoming images, portions of any of said images previous or current responses or portions of said responses).

The actual manner in determining the final set of images to be used during cognitive mapping from the set of original images can be accomplished in a variety of alternative manners. For instance, images might be discarded immediately from the set for any of the reasons mentioned above or they may stay in the set and be shown multiple times after an error has occurred. Similarly, the images can be shown in an order or randomly within a round. The images may also be merely shown randomly, so that two or more images might be repeated before other images are shown at all. Subject's responses may also determine subsequent images to be shown. For example, if a subject has difficulty properly responding to images of articles of clothing then the system can chose not to show new images of articles of clothing.

In practice, patients have been able to acceptably respond to between 20-100 images out of sets of 100-150 images. The size of the set of images to be used in cognitive mapping can vary based on a number of factors. However, if an operator of the system prefers a certain set size then the baseline determination may end once a suitable number of images has been obtained.

Furthermore, in certain embodiments of the present invention it is preferable to identify a baseline index during the baseline determination. The index can be based on, for example, one or a combination of the following; total number of images shown, number of unique images shown, number of images per category shown (e.g. machines, people, actions), total number of errors, type of errors, number of semantic errors, number of hesitations, lengths of hesitations, number of multiple errors for the same image, number of singular errors for a single image, number of consecutive errors, frustration level, frustration level related to likelihood of an error, a percentage or ratio involving any of the above and/or any other relevant data or information. The baseline index can be a simple percentage of, for example, number of errors over total displayed images. The baseline index can also be the result of a complicated proprietary formula for quantifying a subject's ability to perform the task. A baseline index according to certain embodiments of the present invention is substantially based on the number of times a subject makes only one error out of several correct responses for a similar image compared to the number of images having a perfect number of responses.

The present system is often used with subjects who have a tumor or suffered a brain injury, such as a stroke. As such, subjects may have some degree of aphasia. Any degree of aphasia can affect a subject's ability to repeatedly perform a task. For subjects with advanced aphasia the conditions for selecting a proper image set for cognitive mapping can be relaxed. The degree to which the conditions are relaxed can be based, at least in part, on one or more baseline indexes of the subject.

Additionally, a baseline index can be used in order to monitor progress during multiple stimulation sessions. As an example, if after one or more stimulation sessions the subject is subjected to a new baseline determination with a set of images unique from the first set, a baseline index calculated from the first set can be compared to a baseline index calculated from the second set to monitor possible improvement. By calculating multiple baseline indexes, for example multiple pre and/or multiple post stimulation calculation, it is possible to progressively remove factors apart from the progression or recession of a subject's aphasia.

According to certain embodiments of the present invention, during baseline determination the time of speech onset from the time of an image display can be measured. An average and/or range of times for a subject can be measured and/or calculated. For example, an average person responds within 400-700 ms. However, people can fall outside of that range and/or have an extended normal range of responses. This information can be taken in to account when determining if hesitation has occurred during baseline determination and/or during stimulation. The timing can be measured based on a voice recording either in real time or during post processing. In some embodiments the timing can be measured by a dedicated means for determining the speech onset.

While the previous examples and embodiments have been described with respect to recording and measuring audible responses, it is not the case that ever subject is capable of eliciting an understandable and/or recordable audible response. However, the system as described herein works the same when a means for detecting an intent to speak or of responding in a non-audible way is employed. An example would be a sensor in contact with the throat and/or neck of an individual which is sensitive enough to determine an intent of the subject to speak and/or an intended reply. Such modifications for extreme subject cases will be recognizable to those of skill in the art without departing from the scope of the present invention.

According to certain embodiments of the present invention, the baseline determination as described above is performed multiple times (e.g. two or more) prior to cognitive mapping. Said subsequent baseline determinations can be carried out with the same, similar, partially similar, or different sets of initial and/or selected images.

In a system such as described with respect to FIG. 3, a cognitive package 140 can be utilized, for example, away from a TMS system 130 to determine the subject's speech baseline. With a mobile cognitive package 140 as shown, the subject's speech baseline can be determined in, for example, an office or pre-treatment room and then taken in to a room with the TMS system for speech mapping. Another option is to have a stationary cognitive package or other suitable device in a specific location which can determine the subject's speech baseline. That information can then be loaded on to a removable storage medium or can be electronically transferred and loaded in to the mapping system.

In any of the examples above, the system which determines the subject's speech baseline can be completely automated or subject run and not involve any operator input. In such an embodiment, the speech baseline can even be determined by a user at home, for example by utilizing a program installed on or a website accessible by a computer with a web-camera, or by a kiosk.

Once the speech baseline is known and the appropriate information, e.g. response time, cognitive parameters, removal of certain presentation material, notation of subject response, etc. is entered as well as the subject's MT then speech mapping parameters 212 can be set. Although the present FIG. 4 shows the MT being determined prior to the speech baseline, the two steps can be reversed, for example as will be discussed with respect to FIG. 5.

Speech mapping 214 is begun with initial parameters. The initial parameters can be default parameters or they can be based on any or all of the information in the system pertaining to the subject or to a group of subjects. The operator begins mapping using the initial parameters and at the suspected speech area of the brain. Mapping consists generally of stimulating a specific portion of the brain while presenting material to the subject and having the subject attempt to name the material during stimulation, determining if the specific portion which is stimulated is used for speech, tagging the specific portion with the result and then stimulating another specific portion of the brain until an area is sufficiently mapped.

During speech mapping 214 some specific stimulated portions of the brain in the speech area should elicit an effect on speech and others should not. After stimulating several, or more, specific locations, the results should be evaluated 218 to determine if the stimulation is producing desired results in the subject.

TMS can have several different noticeable effects on a subject's cognitive functions. Specifically related to speech, TMS of certain portions of the brain can cause at least some of the following effects which are described in more detail in Corina, D. P., et al. Analysis of naming errors during cortical stimulation mapping: Implications for models of language representation. Brain & Language (2010), doi: 10.1016/j.band1.2010.04.001 which is herein incorporated by reference:

No response errors—The stimulation can cause the muscles that control speech to become inoperative. Often while experiencing this effect during stimulation the subject will try to speak and will recognize that they are unable to form or articulate words. However, immediately before or after stimulation the subject's speech will be normal. The stimulation can also block a subject's recognition of an image or otherwise block them from naming the image. In this event the subject may continue looking at the subject display and not respond in any way to the presentation material.

Switch words or semantic paraphasia—The stimulation can cause the subject to switch or substitute words for each other. For example, the subject can be shown an image of a cat and they might say dog or car during stimulation. The subject may make the substitution unconsciously and be unaware that they mis-spoke or they may acknowledge the switch. As the switching of words is a noticeable effect that a specific portion of the brain is used in speech it is therefore important during the baseline determination to insure that the subject can clearly identify a piece of presentation material. If during the speech baseline determination a picture is shown to the subject multiple times and the subject's response varies then that is a good reason to remove the image so that the switching of words can be clearly detected. For example, if the picture of a soda can is shown multiple times and the subject responses are "soda" once and "can" the next time then the image should be removed.

Neologisms—Similar to the switching of words, the stimulation can also cause the subject to utter incomprehensible, incomplete, stuttered or otherwise blurred words. The stimulated speech result may be similar to the baseline response but in some way noticeably altered. In order to insure that the speech mapping is as accurate as possible, close attention should be paid, either by the operator or a portion of the system, to the relation between the stimulated speech result and the baseline response to detect any noticeable difference. Abnormalities in the subject's overall speech should also be taken in to account. For example, if a subject slurs words or stumbles with works at times during the baseline determination, then just because the subject did not stumble specifically on a certain image during the baseline determination does not necessarily mean that because they stumbled on it during stimulation that that specific portion of the brain is related to speech. In such a scenario it can be beneficial to re-stimulate the specific portion of the brain with the same or different piece of presentation material then or at a later time.

Other speech peculiarities may be noticed during stimulation that should be taken in to account by the operator or system. The operator or system should take in to account all of the responses, compared to the subject's baseline to determine if the speech mapping is effective. During the evaluation of results 216, if for instance none of the stimulations produce an effect and the mapping is not complete 218, then it can be determined if the speech mapping parameters being used are acceptable and/or appropriate 220.

If the determination 220 is that the parameters are acceptable then speech mapping can continue 214 in the same, or preferably in a new location or area. If it is determined that the parameters are not acceptable then new parameters can be set 212 and the speech mapping can be begun 214 in a new, or preferably in the same area. Once speech mapping for the session is determined complete 218 then the speech mapping ends 222.

During cognitive mapping one or more areas and/or regions of the brain are mapped in order to define a volumetric representation of areas of the brain in said areas and/or regions which are responsible for cognitive function and which are not. As described above, it can often be the case that the negative response areas are more accurate than the positive response areas. Additionally, there can be false readings of responses of the subject. Therefore, it in certain embodiments of the present invention specific areas of the brain are stimulated multiple times and the response from each stimulation is recorded.

When stimulating the same spot multiple times, it is often beneficial to spread the multiple stimulations over a period of time to ensure that there is no lingering effect from a previous stimulation of the same or neighboring spot. Additionally, it can be beneficial to stimulate the same spot multiple times while showing different images for one or more of the times.

In order to keep track of the progress of mapping there can be one or more programs or tools to assist the operator. According to certain embodiments of the present invention there is an automated, or manual, tool which tracks the number of times that each location has been stimulated. Additionally, said tool can indicate other data such as the response from each location and/or the actual or relative length of time since the last stimulation and/or the last neighboring stimulation.

The tool can be as basic as a counter for each location, area, region or combination thereof. A basic tool can also comprise a grid which has been automatically generated or drawn by the operator of the system over the anatomical model. The tool can then indicate for areas of the grid, such as, for example, grid boxes, lines, intersections or sectors, the aggregate amount of stimulation. The basic tool may also indicate additional information as discussed above or other information which is of value to the operator of the system. A tool can indicate when a location or area has received an acceptable level of stimulation for verifying the results and/or nearing or reaching a maximum level of stimulation for the area for a certain period of time.

The tool may also be advanced and indicate one or more preferential locations to stimulate next. In certain embodiments of the present invention the tool takes in to consideration past results and data of stimulation of a location, of neighboring locations, and of larger associated areas and regions when determining where to suggest subsequent stimulation. The tool can also take in to consideration the images which have been used and either suggest or automatically chose the image to be displayed at the next indicated location for stimulation.

A tool according to certain embodiments of the present invention can also take in to account previous results in determining if a determination about the involvement of a certain area is verified. For example, as negative responses can be more accurate than positive responses, if an area has, for example, three negative responses then it can be considered verified as having no involvement in the cognitive function. However, the same tool can determine that three positive responses is not sufficient to verify that the area is involved in cognitive function and therefore might require, for example, four positive responses to verify involvement. Additional extensions and variations will be readily apparent. For example, if a location elicits a mixed response, e.g. one negative followed by two positive responses, the tool can indicate that a more thorough testing of the location is necessary. This can also be the case if the area is on an identified boarder region between cognitive and non-cognitive functioning portions of the brain.

A tool may also include an atlas including previous data from previous stimulation and/or post processing of previous stimulation or other means of mapping. Such an atlas can be used to identify specific locations for retesting to, for example, confirm results or check for change/improvement. The tools enumerated herein are merely meant as non-limiting examples of applicable tools. Numerous variations of tools using information available to the system and which can aid in the cognitive mapping process can be utilized which are covered herein and do not depart from the scope of the present invention.

In a partially or fully automated state, a tool as described above can be used to direct some or all of the positioning of the TMS coil or device and/or stimulation during the cognitive mapping.

Figure 5:
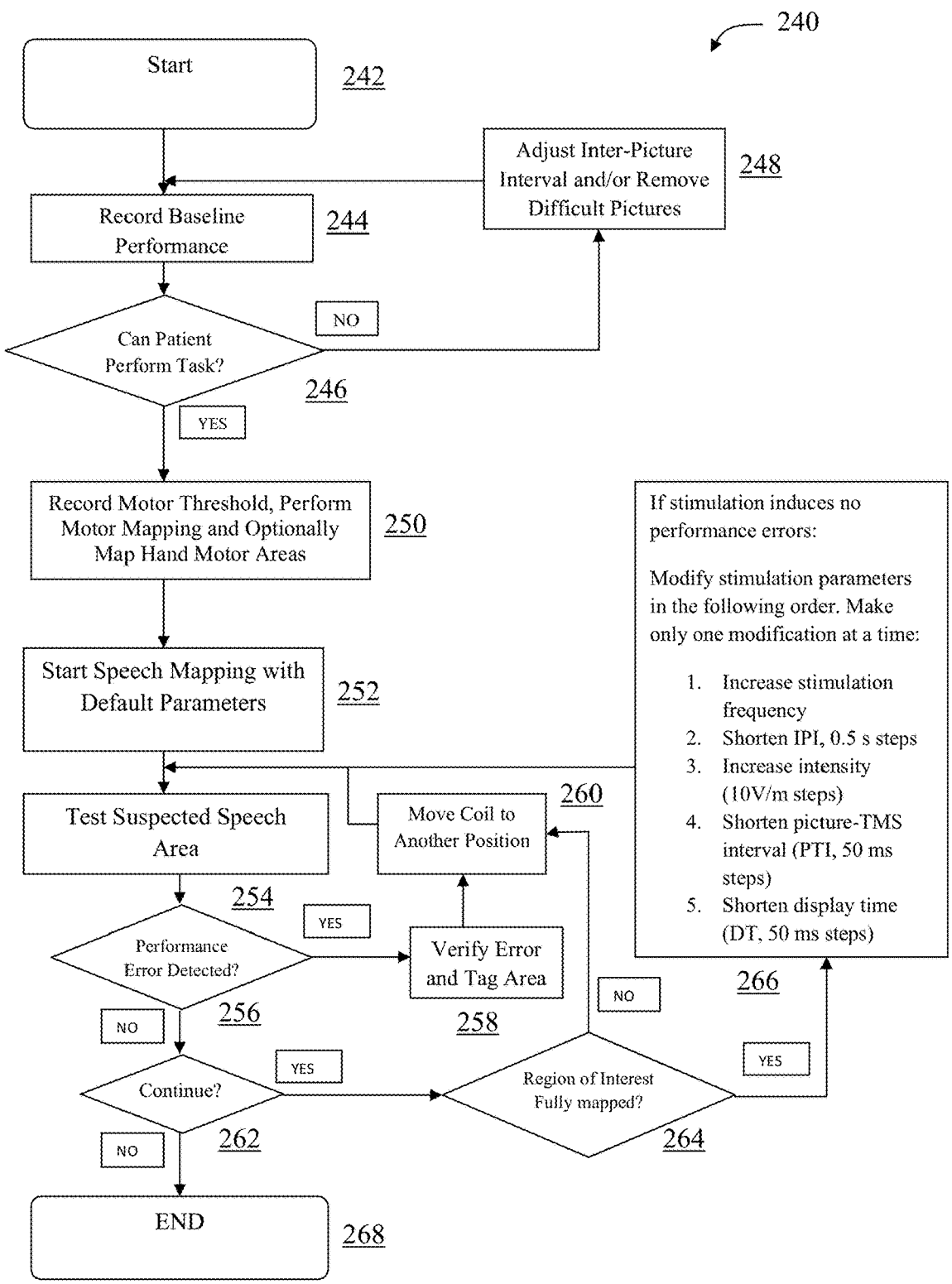
FIG. 5 shows a more detailed flow chart of a method for speech mapping according to an embodiment of the present invention.

FIG. 5 shows an example method 240 for speech mapping similar to method 200 as described with respect to FIG. 4. Upon starting 242 the subject's/patient's baseline performance is recorded 244. In the present example, the subject is shown a series of pictures of objects and is presented with the task of verbally naming the object in the picture as quickly as they can. The subject's responses and response times can be recorded by the operator and/or automatically by one or more cameras and/or microphones.

In one example, each picture is shown for a predetermined length of time after which a black, blank or reference screen is displayed for a second predetermined length of time before the next picture is displayed. In certain embodiments, images can be shown back to back, i.e. without a blank or black image between them. The predetermined length of time that each picture is displayed for is preferably constant and herein referred to as the picture display time. The predetermined length of time between pictures is preferably constant and herein referred to as the inter-picture interval (IPI). Examples of default times are: Interval between consecutive pictures (IPI) in the range of 2-5 seconds, depending on the capacity of the patient to perform the task, display time in the order of 700 ms, and picture to stimulation delay in the range of 200-400 ms.

The subject's ability to perform the task is determined 246 and if the subject is not able to satisfactorily perform the task then at least one parameter of the task is adjusted 248. Examples of a subject's inability to satisfactorily perform the task are their not recognizing one or more pictures at all, not being able to give a clear name for an image, not being able to recognize one or more pictures during the picture display time, not being able to name a picture during the picture display time or combination of picture display time and IPI, becoming stressed by pictures being displayed to quickly or in to rapid a succession, etc. Parameters that can be altered to facilitate the subject's ability to perform the task are adjusting the IPI, the display time and/or removing difficult or troublesome pictures.

While it is preferable that only one parameter is adjusted at a time, multiple parameters can be adjusted simultaneously in step 248. Once the new parameters are set, and preferably recorded, the baseline performance is recorded 244 with the new parameters and it is again determined if the patient can satisfactorily perform the task 246. As discussed above, the baseline task recording is conducted without any brain stimulation. Therefore, parts of, or the entire process can happen away from and/or not connected to a TMS system.

In both the baseline determination as well as during mapping, it can be beneficial to add one or more additionally cues or triggers to the display of an image or to the performance of a task. For example, it can be beneficial to synchronize pictures with breathing and/or blinking. If a picture is shown while a subject is naturally inhaling, blinking or performing some other conscious or unconscious activity it can possibly affect some part of the response, such as the response timing variability. Therefore, according to certain embodiments of the present invention there are cues for an activity, such as breathing or blinking, which are timed with in respect to an image display or task.

Cues can take the form of, for example, audio, visual or tactile cues. A beep, flash on the screen, puff of air, light, pressure, or other type of cue is used to tell the subject to perform a certain action. Then the system can display an image or ask that the subject perform a task at a sufficiently subsequent time where it is clear that the activity will not interfere with the subject's response. These cues can be set at predetermined times or intervals. They may also be initiated by an operator if the operator deems it necessary. Furthermore, the system can automatically detect, through for example audio or video recording, a subject's unconscious activities such as blinking and breathing and time the display of images or tasks accordingly so said activities do not interfere with the responses.

Once the baseline task recording is concluded then the motor threshold can be recorded as discussed previously. Additionally at this point, other TMS processes can be carried out. For instance, motor mapping and/or hand motor area mapping can be performed prior to the speech mapping.

Speech mapping is begun 252 with default parameters. Typical stimulation parameters used as a default are 2-10 pulses at a frequency of 5-10 Hz and an intensity of 90-130% of the subject's MT. For example, 5 pulses at 7 Hz frequency and 120% of MT intensity are well suited for default stimulation parameters. A further example is 7 pulses at 10 Hz. However, suitable parameters can be in the range of, for example 1-100 pulses at frequencies between 1-400 Hz and intensities of 1-120% of the subject's MT. In certain embodiments, high frequency bursts are used in place of single pulses. High frequency bursts can range from 200-1000 Hz and can include from 2 to 10 pulses in each burst. Additionally, the default picture display parameters for stimulation, e.g. picture display time, IPI, etc. should be based on the subject's speech baseline.

Paired pulses (also known as double pulses) or high frequency bursts can be used in order to increase a subject's response to a stimulus or to more effectively interrupt an ongoing cognitive brain processes. The intensity of the first and later pulse(s) of a paired pulse or burst of pulses can be equal, substantially equal, or the first pulse can have a higher or lower intensity than a second or later pulse(s).

Bi-phasic double pulse stimulation can be used in place of a train of RTM stimulation pulses. A bi-phasic double pulse comprises, or consists, of two full sinus waves. Once the first bi-phasic sinus wave pulse is delivered through the stimulation coil then there is delivered a second, bi-phasic sinus wave pulse.

While the second pulse can have classically the same, or greater amplitude, it is been found that it is often preferential for the second pulse to have an amplitude less than the first pulse. Interpulse interval for double pulses is often selected based on expected physiological effects. Typically, short pulse repetition intervals have opposite effects from long repetition intervals. For example, double pulses used in transcranial magnetic stimulation can have can interpulse intervals ranging from, for instance, 1-20 milliseconds, corresponding to repetition frequency of 50 Hz-1000 Hz.

Due to constraints of current technology, there is a short pause in stimulation between the two pulses of a bi-phasic double pulse. The pause is caused in part by the necessity of the first pulse to return through the coil. One constraint on the length of the pause is the speed of any switcher(s) used in the TMS device and/or coil. Another constraint is the amount of time necessary for recharging a capacitor between pulses. The length of the pause is between, for example, 0.1-15 ms. This pause can be reduced or negated as much as physically possible at least in part with the construction of a TMS device with the necessary capacitor or set of capacitors and switcher(s) to release a second biphasic pulse after a first without the need of recharging or of recharging only slightly between pulses. Additionally, a pause having a similar duration, for example 0.1-15 ms, may be designed in to the bi-phasic double pulse if so desired by the operator.

During stimulation using bi-phasic double pulses it is beneficial to begin each pulse at 0, or in a neutral, i.e. not in the positive or negative phase. Examples of the total duration between peak amplitudes of a first and second pulse from a bi-phasic double pulse are 3, 7 and 15 ms. Additionally, examples of the difference between the peak amplitudes of the first and second pulses range from the second pulse being between 5-50% weaker than the first pulse. However, these parameters are merely beneficial and some modification thereof by one of ordinary skill in the art falls within the scope of the present application.

In general, the amplitude of the first pulse can be determined and modified as described above with regards to other means of pulse stimulation. For example, when using bi-phasic double pulses the MT is determined and used as a baseline, and/or guide in determining initial stimulation levels for things like cognitive mapping. One of the benefits of using bi-phasic double pulses is that the amplitude of the first pulse in a bi-phasic double pulse can be between, for example, 15-30% less than the amplitude of one or more mono-phase pulses to elicit the same or greater response for the subject. In some cases, when a subject's mono-phasic stimulation MT is determined, utilizing a bi-phasic double pulse stimulation having the first amplitude of 18-20% less than the subject's mono-phase stimulation MT can elicit responses up to 10 times greater than expected.

Several benefits arise from using bi-phasic double pulses. For example, because the absolute amplitude of the pulses from a bi-phasic double pulse can be less than that required by a similar mono-phasic, or series of mono-phasic pulses, the total exposure for the subject and operator can be limited. Similarly, the reduction of peak amplitude can reduce the temperature increase on cells in the brain. Another example is that the reduced peak amplitude can lessen negative effects of stimulation on surface muscles and the scalp. Furthermore, as the effects of a bi-phasic pulse can be, for example, up to or even greater than 10 times that of a mono-phasic pulse stimulation, the absolute number of pulses during a single stimulation can be decreased giving more time between the end of stimulation and the onset of the subject's speech. This can insure little or no overlap between the subject's speech and stimulation, making the detection of speech onset much easier and more reliable. Further yet, another benefit can be that the greater response elicited by bi-phase double pulses can add a higher degree of reliability to cognitive results, e.g. reduce false negative results.

The use of paired pulses and/or high frequency bursts allow for easier detection of effects from stimulation. One or more of said paired pulses or high frequency bursts can be used in a single set of stimulation pulses as described above with respect to the typical stimulation parameters. Therefore, through their use, an operator can more easily determine if a stimulated region has a speech function.

In many instances, determining if a subject's speech or cognitive function has been altered can be difficult for an operator to detect on their own. Additionally, it can even be difficult or consume to many system resources (processing power, bandwidth, etc.) to efficiently analyze a subject's response to stimulation in real time. Therefore, through the information and data collected by the system, e.g. the video and/or audio recording of the subject during stimulation and during baseline determination, the subject's responses can be analyzed at a later time and/or at a remote location through post analysis.

Picture display parameters for stimulation can be considered as stimulation parameters or as a separate set of parameters. For instance, if the system is being controlled centrally by, for example a terminal 102, then they can be considered a single set of parameters. However, if the control of the system is being share, for example between a terminal 102 and a cognitive package 140, then stimulation parameters may be used with terminal 102 while separate picture display parameters are used with cognitive package 140.

The area suspected of speech function is then tested 254. The area can be chosen by the operator or it can be an area chosen by the system, for example the NBS or navigation software, which is displayed to the operator, for example on operator NBS display 106, to test. The area is then stimulated while a picture is displayed to the subject and it is detected whether there was a performance error by the subject in response to the stimulation 256.

The timing of the stimulation, picture display and response monitoring is important. Several different methods of synchronizing and controlling the process are available. In one method, terminal 102 controls the timing and sends a first trigger to the TMS 108 to produce automatically stimulation via the stimulating device 110. Terminal 102 then causes the subject display 114 to display the desired picture at a time in accordance with the stimulation of the stimulating device 110.

The correlation between the timing of the stimulation and the display of the pictures can be that the stimulation and display begin at the same point in time, or the display begins slightly before or after the beginning of the stimulation. Additionally, the display of the pictures can continue for the same length of time as the stimulation or it can be slightly shorter or longer than the length of stimulation. One example of the correlation of timing is as follows: at time T=0 ms the display onset. At time T=300 ms beginning of the stimulation (PTI=300 ms) and at time T=700 ms the display is off.

Another method that can be utilized is time syncing the necessary elements of the system. If TMS 108 is time synced with at least the cognitive software and the terminal 102 then the terminal 102 can send a message to both the TMS 108 and the cognitive software to stimulate and display at a specific time(s). Such a method works well if the cognitive software is a part of a cognitive package 140.

If the operator is primarily controlling the session, e.g. test location selection, IPI, then the control of the system, e.g. timing control as discussed herein, can be handled by the navigation software. If the cognitive software is controlling the session, e.g. test location selection, IPI, then the control of the system, e.g. timing control as discussed herein, can be handled by the cognitive software. In the latter scenario, if the cognitive software is controlling the session and is located in a cognitive package 140, then the cognitive package can be the primary controller of the system during speech mapping.

While the operator can be responsible for monitoring the subject's responses during mapping and then inputting either the response or an indicator of detected performance error, the monitoring of the subject's responses can be done via the system, e.g. camera 116 or 146. When a recording device is utilized to monitor the subject's responses then the recording device and/or the review/analysis of the recorded material should be coordinated with the stimulation. This can be done by time syncing the recording device and/or the recorded material with other portions of the system, as discussed above. Additionally, the recording device can be activated by a trigger sent by a portion of the system, e.g. terminal 102, the navigation software or the cognitive software. Another method of triggering the recording device can be, for instance, the sound made by the stimulating device 110 during stimulation. The recognition of the sound of the stimulating device 110 can, for instance, initiate recording or can be tagged with the recorded material to indicate that at that point the subject's brain was being stimulated.

If a performance error is detected then the operator can tag the area 258 as being involved with the speech function. If the system detects an error then the system can automatically tag the area as well. When the system is automatically detecting user error, there can concurrently be operator review. For instance, if the system detected an error but the operator was not sure of the error or believe the determined error to be attributed to something besides the stimulation, then operator can override the tagging and/or proceed to retest the site. As long as the result of a stimulation is satisfactory then the operator will move the stimulation device 110 to a new position 260 and perform the stimulation again to test the next suspected speech area.

In an embodiment, the cognitive program controls the flow of the speech mapping. The cognitive program sets the IPI and indicates to the operator, through a display, where the next suspected speech area is and when the next stimulation will occur. In such an embodiment, while the operator can be able to override the set flow, their main function is to properly align the stimulation device according to the NBS display 106 in sufficient time for the next scheduled stimulation. The cognitive program can have a predetermined set of points, e.g. predetermined grid, which the operator is to follow in succession or via another set order. The cognitive program may also select either the order or the specific location of the next stimulation based on results of at least one of the previous stimulations.

Once the stimulation has occurred and no performance error is detected 256 then it is determined, either by the operator or a portion of the system, if the desired region is fully mapped 262. In order to fully map an area of the brain for speech, the region of interest in the brain should contain a set of tagged locations indicating locations relevant to speech surrounded by several tagged locations indicating that the locations are not relevant to speech. Therefore, if no performance error is detected and the region of interest is not fully mapped 264 then the process continues by stimulating another position.

In some instances, it can be determined in step 264 that no performance error was detected, that the region of interest was fully mapped but that the speech mapping was not complete. For instance, if the region of interest is believed to be relevant to speech but no performance error has been detected, then the problem may lay in the stimulation parameters being used. In this case then one or more of the stimulation parameters are altered and an area, often one of the same previous areas, is tested again.

Some of the stimulation parameters that can be modified if no performance error is detected in an area which should be relevant to speech can be selected from the stimulation frequency, IPI, stimulation intensity, TMS interval, Picture TMS interval (PTI), pulse mode, pulse number and/or picture display time. It is preferable that when modifying stimulation parameters that only one parameter is modified at a time. Furthermore, it is preferable that parameters are altered in the order as shown in step 266 of FIG. 5.

In an embodiment according to FIG. 5, the first time that it is determined in step 264 that a stimulation parameter is to be modified in step 266, the stimulation frequency is increased. The amount which the stimulation frequency is increased can vary based on the remainder of the current parameters or by a predetermined amount. An example is that the first frequency increase can be 5 Hz and may increase to 7 Hz to 10 Hz. If the process continues and there is again determined after some number of testings at step 264 that the stimulation parameters are still not adequate, then the frequency can be increased again, or the next parameter, in the present example the IPI, can be adjusted.

In the present example, the chain of stimulation parameters to be adjusted is increasing the stimulation frequency, then shortening the IPI (for example by 0.5 seconds), then increasing the intensity (for example by a percentage of the subject's MT or by a predetermined amount such as 10V/m), then shortening PTI (for example by 50 ms) and finally by shortening the display time of the picture (for example by 50 ms). The chain can be done sequentially, i.e. the first time increasing the frequency, the second time shortening the IPI, the third time increasing intensity, the fourth time shortening PTI, the fifth time shortening display time, the sixth time increasing frequency, the seventh time shortening IPI, and so on.

The chain can also be carried out in stages where the frequency is increased a predetermined amount of times, or to a predetermined limit and then the chain moves to the next stage of shortening the IPI by a predetermined amount of times, or to a predetermined limit and so on. Although it is preferable to only make one modification at a time, when carrying out the chain in stages, it can be beneficial if the frequency begins at a certain first level, to increase it sequentially to a limit (or a predetermined number of times) and then to decrease the frequency below the limit but to a level above the first level and then to proceed by adjusting the next parameter and so on.

The chain described herein is only an example and modifying the stimulation parameters in other ways not explicitly described herein does not depart from the scope of the present invention. Once the stimulation parameters are properly set and the area of the brain that is to be mapped during that particular session is determined completed 262 then the speech mapping ends 268. At this point, the mapping data can be saved or loaded in to a hard drive in the system, for instance in a non-transitory computer readable storage medium on terminal 102 or 142. Additionally, the mapping data, with or without additional information such as the MT, speech baseline, stimulation parameters, etc., can be loaded on to an external or removable hard drive or on to a remote server. Said information can then be utilized later by the same or another system to re-map, review or otherwise utilize the data.

The present invention is not limited to the examples and embodiments disclosed herein. Numerous variations and embodiments not explicitly disclosed herein will be apparent to those of ordinary skill in the art without departing from the scope of the present invention.

The invention claimed is:

1. A method of cognitive mapping using a Navigated Brain Stimulation (NBS) system, said NBS system comprising: a Transcranial Magnetic Stimulation (TMS) coil device and a tracking system for determining the location of the TMS coil device in relation to the brain of a subject, said method comprising the steps of;

determining a cognitive base line speech response for a cognitive speech function from a subject in response to a presentation of a task, presenting the task to the subject again while stimulating an area of the brain with a magnetic field via the TMS coil device, said area being determined and stored by the NB S system, recording a speech performance of the subject during stimulation with at least one of: a microphone and camera, comparing the subject's base line speech response to the task with the subject's performance during stimulation, and based at least partially on the comparison, determining if the area of the brain stimulated is involved in the cognitive speech function and if the area of the brain is involved in the cognitive speech function, tagging the location within the NBS system, wherein the TMS coil device is operated with a set of parameters, wherein the set of parameters includes a picture TMS interval (PTI) of 10 ms to 1.5 sec.

2. A method in accordance with claim 1, further comprising the steps of;

presenting the task to the subject one or more further times while correspondingly stimulating one or more further areas of the brain with at least one additional magnetic field via the TMS coil device, comparing the subject's base line response to the task with each of the subject's performances during stimulations, and determining if one or more of the areas of the brain stimulated are involved in the cognitive function.

3. A method in accordance with claim 2, wherein comparing the subject's base line response to the task with each of the subject's performances during stimulations is done automatically by a cognitive package.

4. A method in accordance with claim 1, wherein;

when presenting the task to the subject while stimulating the area of the brain with the magnetic field via the TMS coil device a first set of stimulation parameters is used, and if no performance error is detected between the base line speech response and the subject's performance during stimulation, at least one parameter of the first set of stimulation parameters is changed, the method further comprising the step of:

presenting the task to the subject while stimulating the same area of the brain with an additional magnetic field via the TMS coil device with the new set of stimulation parameters.

5. A method in accordance with claim 4, wherein the set of parameters are selected from the group of stimulation frequency, inter picture interval, stimulation intensity, picture, TMS interval, pulse mode, number of pulses and task display time.

6. A method in accordance with claim 4, wherein if no performance error is detected between the subject's performance during stimulation with the new set of parameters, changing at least one parameter of the new set of parameters and presenting the task to the subject while stimulating the same area of the brain with the magnetic field via the TMS coil device with the updated new set of parameters.

7. A method in accordance with claim 6, wherein the method is repeated until it is determined that the area being stimulated is not involved in the cognitive function.

8. A method in accordance with claim 1, wherein the stimulated area of the brain is three dimensionally pre-mapped and the area of the brain which is stimulated is a specific point on the surface or within the subject's brain.

9. A method in accordance with claim 8, wherein the subject's cognitive function is mapped on a model of a brain selected from a standard brain model, a brain model equivalent to the subject's brain or a brain model specific to the subject's brain.

10. A method in accordance with claim 9, wherein the subject's cognitive function is mapped on a model of the brain specific to the subject which is at least partially based on an MRI of the subject's brain.

11. A method in accordance with claim 1, wherein the task is presenting a series of images, sounds, and/or questions to the subject and having the subject respond to each presentation.

12. A method in accordance with claim 1, wherein determining if the area of the brain stimulated is involved in the cognitive function is done automatically by a cognitive package.

13. A method in accordance with claim 1, further comprising the step of determining a motor threshold or speech arrest threshold of the subject prior to stimulating the subject's brain via the TMS coil device.

14. A method in accordance with claim 13, wherein the TMS coil device is operated with a set of parameters, wherein the set of parameters includes the stimulation intensity of 1-110% of a subject's motor threshold or speech arrest threshold.

15. A method in accordance with claim 1, wherein the TMS coil device is operated with a set of parameters, wherein the set of parameters includes a number of stimulation pulses between 1 and 100.

16. A method in accordance with claim 1, wherein the TMS coil device is operated with a set of parameters, wherein the set of parameters includes a pulse frequency between 1 and 100 Hz.

17. The method of claim 1 wherein the NBS system provides indications of previously stimulated areas within the subjects brain in order to guide the mapping.

18. The method of claim 1 wherein the tracking system comprises tracking markers attached to the TMS coil device.

19. A system for cognitive mapping comprising;

a Transcranial Magnetic Stimulation (TMS) coil device, a stimulus control connected to said TMS coil device capable of causing said TMS coil device to generate a magnetic field, a tracking system configured to determine a location of the TMS coil device in relation to the brain of a subject and thus determine a location within the brain of an individual which would be stimulated by a magnetic field generated by the TMS coil device, a presentation display for presenting a task to the subject, at least one of: a microphone and camera, at least one terminal having one or more processors, said one or more processors being configured to perform the steps of:

determining, recording and/or inputting a cognitive base line speech response from the subject in response to the presentation of the task, presenting the task to the subject via the presentation display while stimulating an area of the brain with the magnetic field via the TMS coil device said area being determined and recorded by the tracking system, determining or recording a speech response from the subject in response to the presentation of the task during stimulation, comparing the subject's base line response to the task with the subject's speech response during stimulation, and determining if the area of the brain stimulated is involved in a cognitive speech function associated with the presentation of the task, based at least partially on the comparison, and if the area of the brain is involved in the cognitive speech function, tagging the location determined by the tracking system said tag being stored within the terminal, wherein the TMS coil device is operated with a set of parameters, wherein the set of parameters includes a picture TMS interval (PTI) of 10 ms to 1.5 sec.

20. A system in accordance with claim 19, wherein at least one or more of the processors are further configured such that;

when presenting the task to the subject while stimulating the area of the brain with the magnetic field via the TMS coil device a first set of stimulation parameters is used, and if no performance error is detected between the subject's base line speech response and the subject's performance during stimulation, at least one of the parameters of the first set of stimulation parameters is changed, at least one or more of the processors being further configured to perform the step of:

presenting the task to the subject while stimulating the same area of the brain with an additional magnetic field via the TMS coil device with the new set of stimulation parameters.

21. A system in accordance with claim 19, further comprising one or more processors configured to perform navigated brain stimulation.

22. A system in accordance with claim 19, further comprising a monitoring device configured to monitor the subject's physical response to stimulation.

23. A system in accordance with claim 19, wherein comparing the subject's base line response to the task with the subject's speech response during stimulation includes comparing the subject's response to a particular task recorded by said at least one of: a microphone and camera during a baseline determination and the subject's response recorded by said at least one of: a microphone and camera during stimulation.

24. A system in accordance with claim 19, wherein the at least one of a microphone and camera comprises a camera which is capable of recording the subject's responses to the presented task, and wherein a feed from said camera is coordinated with the stimulation applied to the subject, said coordination being a time-sync.

* * * * *